(12) United States Patent
Broaddus et al.

(10) Patent No.: US 8,211,083 B2
(45) Date of Patent: Jul. 3, 2012

(54) COAXIAL CATHETER SYSTEMS FOR TRANSFERENCE OF MEDIUM

(75) Inventors: William C. Broaddus, Midlothian, VA (US); Zhi-Jian Chen, Glen Allen, VA (US); George T. Gillies, Charlottesville, VA (US)

(73) Assignees: University of Virginia Patent Foundation, Charlottesville, VA (US); Virginia Commonwealth University Intellectual Property Foundation, Richmond, VA (US)

( * ) Notice: Subject to any disclaimer, the term of this patent is extended or adjusted under 35 U.S.C. 154(b) by 29 days.

(21) Appl. No.: 12/760,837

(22) Filed: Apr. 15, 2010

(65) Prior Publication Data
US 2010/0198137 A1 Aug. 5, 2010

Related U.S. Application Data

(63) Continuation of application No. 11/191,676, filed on Jul. 28, 2005, now Pat. No. 7,727,225.

(60) Provisional application No. 60/591,614, filed on Jul. 28, 2007.

(51) Int. Cl.
*A61M 31/00* (2006.01)

(52) U.S. Cl. ............... 604/506; 604/28; 604/522
(58) Field of Classification Search ............ 604/35, 604/43, 27–28, 158, 164.02, 500, 506–510, 604/513, 522, 540, 542
See application file for complete search history.

(56) References Cited

U.S. PATENT DOCUMENTS 3,081,770 A * 3/1963 Hunter ................... 600/431
7,179,232 B2 * 2/2007 Sutton et al. ............ 600/567

* cited by examiner

*Primary Examiner* — Theodore Stigell
(74) *Attorney, Agent, or Firm* — Robert J. Decker; Kilpatrick Townsend & Stockton LLP

(57) ABSTRACT

A method, technique and system is disclosed for the delivery of therapeutic agents and/or into the bulk brain tissues and other parts, tissues and organs of the body, including vasculature. A novel form of coaxial catheter provides a means for implanting an outer tube into the brain, then inserting an inner tube into the outer tube and aligning them such that port holes on both of the tubes will overlap and permit a flux of the therapeutic agent to flow into the brain in such a way as to minimize the effects of trapped air, virtually eliminate backflow of the agent, and avoid the potential for additional damage to the brain since only one surgical placement of the outer tube is needed. Similarly, the method, technique system may be utilized to remove fluids or other medium from the brain, tissues, and organs to minimize the effects of escaped air or negative pressure.

29 Claims, 7 Drawing Sheets

COAXIAL CATHETER SYSTEMS FOR TRANSFERENCE OF MEDIUM

CROSS-REFERENCES TO RELATED APPLICATIONS

The present application is a continuation application of U.S. patent application Ser. No. 11/191,676, filed Jul. 28, 2005, which claims priority from U.S. Provisional Patent Application Ser. No. 60/591,614, filed Jul. 28, 2004, entitled "Coaxial Catheter Systems for Intraparenchymal Delivery Of Therapeutic Agents," the disclosures of which are hereby incorporated by reference herein in their entirety.

The present Application is also related to: U.S. patent application Ser. No. 10/444,884, filed May 23, 2003 (U.S. 2003/0204171, published Oct. 30, 2003); U.S. Pat. No. 6,599,274; and U.S. patent application Ser. No. 11/105,166, filed Apr. 13, 2005, of which all of the disclosures are hereby incorporated by reference herein in their entirety.

BACKGROUND OF THE INVENTION

There are many instances in which a neurosurgeon or other clinician would wish to deliver a therapeutic or diagnostic agent into the brain of a patient, for example, for the treatment of primary malignant brain tumors. One type of such tumor, glioblastoma multiforme, is a lethal malignancy of the central nervous system that has proven stubbornly resistant to the development of any form of satisfactory therapy that can either halt the advance of the disease, reverse it, or cure it. Anticancer therapies that are often efficacious in other regions of the body, such as chemotherapies, are largely ineffective against diffuse neoplasms in the brain in part because of the presence of the blood-brain barrier. Even in the case where the blood-brain barrier is "leaky" within the tumor bed of a glioblastoma multiforme, regional delivery into the peri-tumoral region (which often harbors invading cells) in which the chemotherapies, gene therapies, and other agents are targeted is hampered by the intact blood-brain barrier in that region, thus making such approaches unworkable. A means of circumventing such delivery problems is offered by the positive pressure infusion of agents directly into the bulk brain tissues, as taught by several workers, examples of which are: U.S. Pat. No. 5,720,720 to Laske, et al., U.S. Pat. No. 6,026,316 to Kucharczyk, et al., and U.S. Pat. No. 6,272,370 to Gillies, et al., of which all of the disclosures are hereby incorporated by reference herein in their entirety. The resulting convection-enhanced flow of infusates through the interstitial space of the brain can provide for regional volumes of distribution of therapeutic agents without the need to have large-molecular weight species traverse the blood-brain barrier. Often, special neurocatheters optimized for this approach to drug delivery are needed to maximize the utility of such therapies. This general approach to intraparenchymal therapies also applies to the delivery of autologous stem cells into the brain for the treatment of neurodegenerative disorders, and for the infusion protocols for the assessment and treatment of traumatic brain injury. Moreover, positive pressure infusion of therapeutic agents and diagnostic into other parts or ducts of the body, including the vasculature, is also practiced routinely within the field of medicine.

Specialized multi-lumen neurocatheter systems have been disclosed by Kucharczyk et al. in U.S. Pat. Nos. 6,599,274 and 6,626,902, of which both of the disclosures are hereby incorporated by reference herein in their entirety. Coaxial catheters for the delivery of cells into the brain have been disclosed by Kucharczyk et al. in U.S. Pat. No. 6,599,274.

Several clinical and pre-clinical applications of various types of neurocatheters are discussed in the following publications: Chen, Z.-J., et al., "Intraparenchymal Drug Delivery via Positive Pressure Infusion: Experimental and Modeling Studies of Poroelasticity in Brain Phantom Gels," *IEEE Transactions on Biomedical Engineering,* 49 (2), 85-96, (February 2002), and Broaddus, W. C., et al., "Advances in Image-Guided Delivery of Drug and Cell Therapies into the Central Nervous System," *Neuroimaging Clinics of North America,* 11 (4), 727-735, (November 2001), of which all of the disclosures are hereby incorporated by reference herein in their entirety.

One limitation of the art is that none of the catheters that have been developed to date, nor those foreseen in the literature but not yet implemented, have been optimized in design for the complete elimination of reflux of the infused agent along the catheter insertion track or within the device structure (particularly if a multi-lumen system is used). The elimination of such reflux would be a desirable feature, especially in instances where the infusate might consist of highly specialized and difficult to obtain agents such as certain kinds of antisense constructs (see Broaddus, W. C., et al., "Strategies for the Design and Delivery of Antisense Oligonucleotide in Central Nervous System," *Methods in Enzymology: Antisense Technology, Part. B: Applications,* 314, 121-135 (2000), which disclosures is hereby incorporated by reference herein in its entirety), but is generally desirable for the optimal delivery of any type of diagnostic or therapeutic agent.

A second limitation of the existing art is that the various types of multi-lumen implantable devices fail to include a suitable flush line to void the internal components of the catheter of any residual amounts of a therapeutic (or other) agent that might remain in them after an initial use, but which should best be removed prior to an additional use, as may be performed with a multi-functional catheter, such as those disclosed in U.S. Pat. No. 6,026,316 to Kucharczyk; and U.S. Pat. No. 6,626,902 to Kucharczyk et al., which are incorporated herein by reference in their entirety.

A third limitation of the art is that the existing multi-lumen catheter designs do not allow simultaneous escape of trapped air and sealing against inter-tube leakage when an inner lumen is inserted into an outer lumen of such a device.

A fourth limitation of the existing art is that the intra-tube flow dividers inside the inner tube of multi-lumen devices seal at the end of the catheter in such a way that there cannot be communication between what could otherwise function as infusion and flushing channels.

A fifth limitation of the existing art is that many types of existing multi-lumen, multi-port hole catheters require the use of an internally inflatable balloon to either enable the drug delivery or port hole selection process. Examples of such devices and associated methods are those taught by Baran et al. in U.S. Pat. No. 4,423,725, Schweich et al. in U.S. Pat. No. 5,716,340 and Lary in U.S. Pat. No. 6,506,180, of which all of the disclosures are hereby incorporated by reference herein in their entirety. A general discussion of clinical applications of multi-port hole catheters for imaging of intravascular gene therapy has been presented by Xiaoming Yang, "Imaging of Vascular Gene Therapy," *Radiology,* 228 (1), 36-49 (July 2003), of which the disclosure is hereby incorporated by reference herein in its entirety. Other publications that are incorporated by reference herein in their entirety including the following: Broaddus, W. C., Gillies, G. T., and Kucharczyk, J., "Image-Guided Intraparenchymal Drug and Cell Therapy," in Latchaw, R. E., Kucharczyk, J., and Moseley, M. E., eds., *Imaging of the Nervous System: Diagnostic and Therapeutic Applications,* Vol. 2 (Elsevier-Mosby, Philadelphia, 2005), Chap. 72, pp. 1467-1476; Chiocca, E. A., Broaddus, W. C., Gillies, G. T., Visted, T., and Lamfers, M. L. M., "Neurosurgical Delivery of Chemotherapeutics, Targeted Toxins, Genetic and Viral Therapies in Neuro-Oncology," *Journal of Neuro-Oncology*, 69, 101-117, (2004); Gillies, G. T., Smith, J. H., and Humphrey, J. A. C., "Positive Pressure Infusion of Therapeutic Agents into Brain Tissues: Mathematical and Experimental Simulations," in Yamaguchi, T., ed., *Frontiers of Medical Informatics: Proceedings of the 4th International Symposium on Future Medical Engineering Based on Bio-Nanotechnology* (21st Century COE Program), (Tohoku University, Sendai, Japan, 2004), pp. 7-12; and Bauman, M. A., Gillies, G. T., Raghavan, R., Brady, M. L., and Pedain, C., "Physical Characterization of Neurocatheter Performance in a Brain Phantom Gelatin with Nanoscale Porosity: Stead-State and Oscillatory Flows," *Nanotechnology*, 15, 92-97, (2004).

None of the multi-lumen intraparenchymal therapy delivery devices existing in the art traverse these limitations, nor does the prior art teach or suggest means, techniques and systems for improving the designs of them such that these limitations would not prevent successful diagnostic and therapeutic protocols from being carried out.

Significant and potentially useful advances in the treatment of glioblastoma multiforme, traumatic brain injury, neurodegenerative disorders and many other neurological and neurosurgical indications could be realized if alternatives to the prior art were able to demonstrate safety and efficacy via improvement of the catheter systems used for therapy delivery. The various embodiments of the present invention disclose a means, technique and system for attempting to reach this goal by implementation of a novel set of catheter structures, functions and means that traverse the limitations of the existing art discussed above and elsewhere.

SUMMARY OF THE INVENTION

Various structures, materials and practices described herein, some of which constitute embodiments of a proprietary invention, provide at least some of: an improved means of delivering therapeutic and diagnostic agents into the brain for the assessment and treatment of sequellae of traumatic brain injury; the diagnosis and treatment of intracranial neoplasms; the investigation and counteraction of neurodegenerative disorders; and generally for the neurosurgical evaluation and treatment of neurological insults, injuries, diseases and syndromes. Moreover, various embodiments described herein as a proprietary method and system provide an improvement in the field of implantable medical devices and neurocatheters in particular. Still yet, various embodiments described herein as a proprietary method and system provide an improvement in the field of neurocatheters that can be used to carry out positive pressure infusions of therapeutic agents into the brain, particularly for the purpose of avoiding the screening effects of the blood-brain barrier. Additionally, various embodiments described herein as a proprietary method and system provide an improvement in the field of neurocatheters that are multi-lumen devices. Further, various embodiments described herein as a proprietary method and system provide an improvement regarding treatment that requires successive delivery of initial and follow-up doses of therapeutic agents, or successive delivery of a first and then subsequent different therapeutic agents, into the same location or set of locations within a brain of a patient. Various embodiments described herein as a proprietary method and system additionally improve the ability to the use of multi-lumen catheters in body parts, ducts, tissues and organs other than the brain, including the vasculature.

Various embodiments of the technology, described herein as a proprietary method, structure, apparatus and/or system, provide a capability or means for delivering therapies into the bulk brain tissues or other body parts or ducts, including the vasculature, using a novel arrangement of coaxial catheters that constitute a single implantable medical device. A structure, system or means for accomplishing this may include a catheter with a fixed number of port holes that is inserted into a brain (or other region of the anatomy) of a patient or subject using any format of imaging and guidance deemed appropriate by the neurosurgeon or interventionalist caring for the patient. Such insertion format, procedure or means might include, but not be limited to, any kind of stereotactic system and procedure, or any kind of magnetic-resonance-based trajectory guidance. The catheter may constitute the outer tube of a multi-tube coaxial system. Then, a second catheter with a particular arrangement of port holes is inserted into the inside of the barrel of the outer catheter. The second catheter is then referred to as the inner catheter of this multi-tube coaxial system. In an embodiment, the inner catheter may have components constituting a sealing system, such as a kind of sealing gasket located around its circumference above and below the port holes in it. In another embodiment, the outer catheter may have components constituting a kind of sealing system such as a sealing gasket located around its inner circumference above and below the port holes in it. The port holes on the inner catheter may be arranged to allow communication with the internal chambers of the inner catheter. An illustrative example of medium communication and control may be provided by referring to U.S. Pat. No. 6,464,662 B1 to Raghavan et al., U.S. patent application Ser. No. 10/444,884 to Kucharczyk et al., filed May 23, 2003, U.S. Pat. No. 6,599,274 to Kucharczyk et al., and U.S. patent application Ser. No. 11/105,166 to Kucharczyk et al., filed Apr. 13, 2005, of which all of the disclosures are hereby incorporated by reference herein in their entirety. Fluids can be pumped through the internal chambers of the inner catheter and exit through the port holes in its wall. When the inner catheter is inserted and aligned within the outer catheter such that the port holes on the two tubes are congruent with each other, the fluid (for example, a diagnostic or therapeutic agent) or applicable medium can then be delivered through the sequence of port holes into a brain of a patient. The gasket or sealing means in either class of design will seal the inter-tube passage way (gap) such that none of the therapeutic agent can reflux through the inter-tube passage way (gap). Any air trapped within the outer catheter during the insertion of the inner catheter can escape through a channel on the inside of the inner catheter via a distal-end opening on the inner catheter that communicates with the internal channel of the inner catheter for that purpose. Friction-fit, elastic conformance, threaded, bayoneted, tabbed or other types of locking mechanisms in the hub of the outer catheter will allow fixation of the inner catheter relative to the outer catheter at desired axial and circumferential positions that will ensure proper alignment of the port holes on both tubes. One or more internal chambers of the inner catheter may serve as flush lines for voiding the inner catheter of one type of infused agent before beginning the process of delivering a second type of infused agent. Likewise, the flushing mechanism and/or inner catheter can also be employed for protocols in which fluids or applicable medium are being withdrawn from a brain of a patient or from a different body part or duct, including the vasculature. Volume contoured delivery of diagnostic and therapeutic agents, i.e., the creation of volumes of distribution that are adjusted to the geometry of the lesion or target location being treated, will be possible using this device, simply by relocating the inner catheter relative to the outer catheter, for example during the course of an infusion protocol. Delivery of a sequence of agents into desired locations within a brain or some other body part or duct, including the vasculature, of a patient will be possible without reinsertion of the outer catheter through the brain or other tissues or vasculature by simply flushing the inner catheter and then reusing it, or by withdrawal of a given inner catheter and insertion of another inner catheter into the fixed-position outer catheter. Magnetic resonance spectroscopy of the region of the brain surrounding the tip of the catheter could be carried out via the placement of appropriate microcoils at locations on the distal end (as well as other desired locations) of the outer catheter.

An aspect of an embodiment of the present invention system provides a catheter or similar device for transferring at least one medium with a subject. The catheter or similar device having a distal end and a proximal end. The device comprising: an outer tube having a distal end and a proximal end, and having a wall extending longitudinally there between; an inner tube disposed within the outer tube, the inner tube having a distal end and a proximal end, and having a wall extending longitudinally there between defining a inner tube flow area for transference of the medium; a longitudinal space between the outer tube and inner tube defining an inter-tube gap; at least one outer tube aperture disposed on the outer tube wall; at least one inner tube aperture disposed on the inner tube wall; the inner tube being adapted to move longitudinally and/or circumferentially relative to the outer tube to provide for the at least one inner tube aperture to be in communication with the at least one outer tube aperture to allow transference of the medium between the inner tube and the subject; and a sealing system disposed in the inter-tube gap to control the medium from traveling within the inter-tube gap.

An aspect of an embodiment of the present invention provides a method for delivering at least one medium to a subject using a catheter or similar device. The method comprises: inserting an outer tube into the subject, the outer tube having a distal end and a proximal end and comprising at least one aperture there between; disposing an inner tube within the outer tube, the inner tube having a distal end and a proximal end and comprising at least one aperture there between; providing the at least one medium to the inner tube; and aligning the outer tube aperture and the inner tube aperture to allow the at least one medium to travel through the inner tube aperture and outer tube aperture to the subject while controlling the medium from traveling between the exterior of the inner tube and interior of the outer tube. Additionally, the method may further comprise withdrawing a medium from the subject by aligning the outer tube aperture and the inner tube aperture to allow the at least one medium to travel from the subject through the outer tube aperture and inner tube aperture to the inner tube while controlling the medium from traveling between the exterior of the inner tube and interior of the outer tube.

An aspect of an embodiment of the present invention provides a method for withdrawing at least one medium to a subject using a catheter or similar device. The method comprising: inserting an outer tube into the subject, the outer tube having a distal end and a proximal end and comprising at least one aperture there between; disposing an inner tube within the outer tube, the inner tube having a distal end and a proximal end and comprising at least one aperture there between; and aligning the outer tube aperture and the inner tube aperture to allow the at least one medium to travel from the subject through the outer tube aperture and inner tube aperture to the inner tube while controlling the medium from traveling between the exterior of the inner tube and interior of the outer tube.

These and other aspects of the disclosed technology and systems, along with their advantages and features, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 6(A) provides a schematic elevational view from the distal end an embodiment of an inner catheter in which the interior of the inner catheter has been divided along its axial length into a plurality of chambers or the like.

DETAILED DESCRIPTION OF THE DRAWINGS

Figure 1:
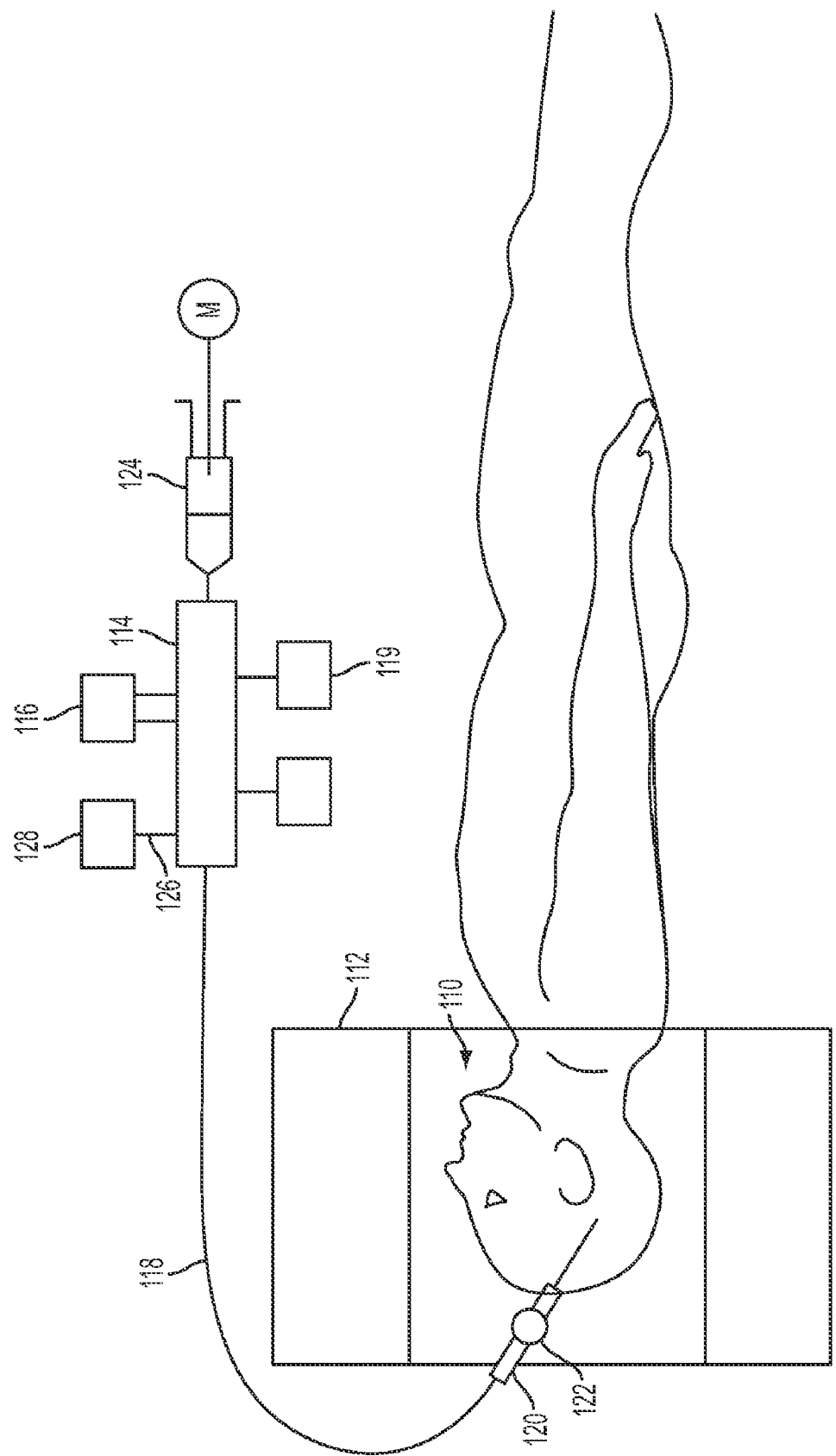
FIG. 1 is a schematic diagram showing a patient, or any subject or object, undergoing an examination and/or intervention in an MRI magnet whereby a catheter device is disposed within the patient.

FIG. 1 is a schematic diagram showing a patient 110, or any subject or object, undergoing an examination and/or intervention inside the bore of an MRI system 112 whereby a catheter device is disposed within the patient. A manifold 114 couples several therapeutic or diagnostic devices typified by device 116 to the cell delivery catheter 118. A syringe, flow-driver or pumping device 124 is also in communication with the manifold 114. The cell delivery catheter 118 in turn may be delivered through a guide sheath 120 that may be positioned in a navigation guide 122. In operation the physician or user inserts the catheter device 118 into the brain (or other anatomy part or subject region) under MRI guidance or other applicable examination or intervention. The same or similar MRI visualization may be used to follow the progress of the implant both acutely and chronically. This specific version of the catheter within the generic concepts disclosed herein may have an outer catheter/tube with an inner catheter/tube within that will be described in greater detail herein. This catheter device may have various interior and peripheral lumens, chambers and channels that will also be discussed in greater detail herein, within the context of the generic disclosure provided. Such interior and peripheral lumens, chambers and channels may be used to deliver other devices and perform various diagnostic functions. For example, each lumen, chamber, and channel may communicate with a separate port of the manifold 114. A lumen, chamber or channel may contain a pressure transducer 128. Other lumens and channels may be devoted to an optical cell counter device, for example, as shown generically as device 119 in FIG. 1. Such a device may operate with two fibers located in two separate lumens and/or ports to measure the number of and viability of cells delivered by the catheter. An example of fiber optics related application/technology is discussed in U.S. patent application Ser. No. 10/444,884, filed May 23, 2003 (U.S. 2003/0204171, published Oct. 30, 2003).

It should be appreciated, that as discussed herein a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog), etc. It should be appreciated that the subject may be any applicable patient, for example.

Figure 2:
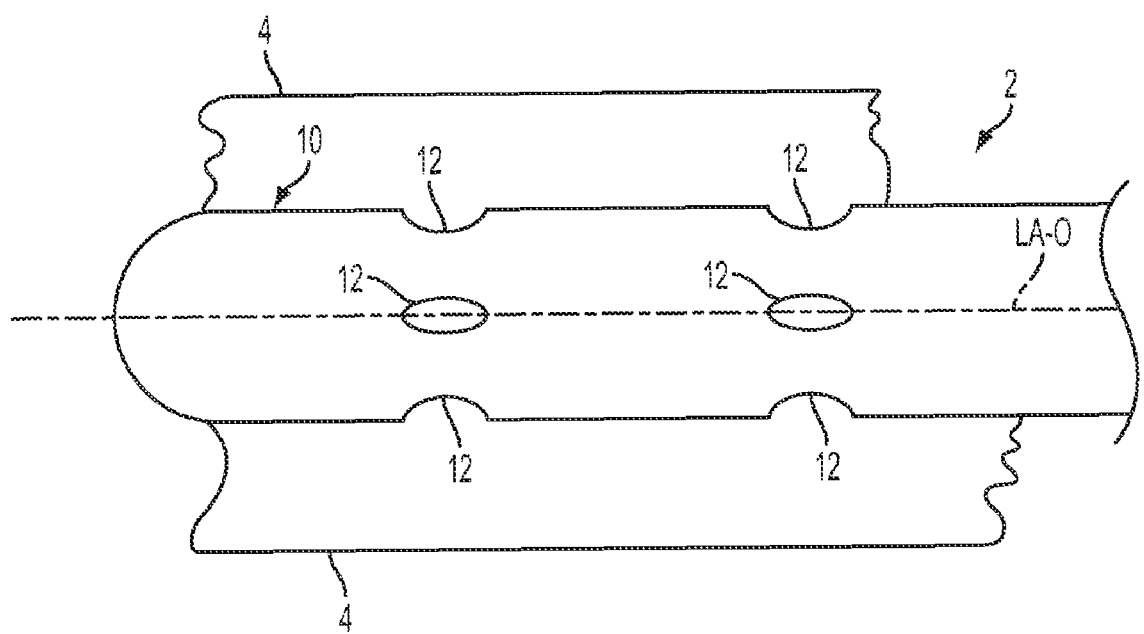
FIG. 2 is a schematic elevational view of a portion of a catheter having an outer catheter or outer tube which has an empty inner barrel into which inner catheter or inner tube (not shown) can be inserted, removed, translated and/or rotated therein.

FIG. 2 is a schematic elevational view of a portion of a catheter 2 having an outer catheter 10 or outer tube which has an empty inner barrel into which inner catheter 30 or inner tube (not shown) can be inserted, removed, translated and rotated during the course, for instance, of neurosurgical or neurointerventional procedures. The outer catheter 10 or outer tube has an arrangement of apertures 12 such as a port hole means placed in its wall 14 in an appropriate or desired pattern. In one specific embodiment as shown here, the port holes 12 are in a circumferential arrangement, with at least three sets of them located along the longitudinal axis, LA-O, of the outer catheter 10. The apertures 12 may be arranged and located circumferentially and longitudinally as required.

Figure 3A:
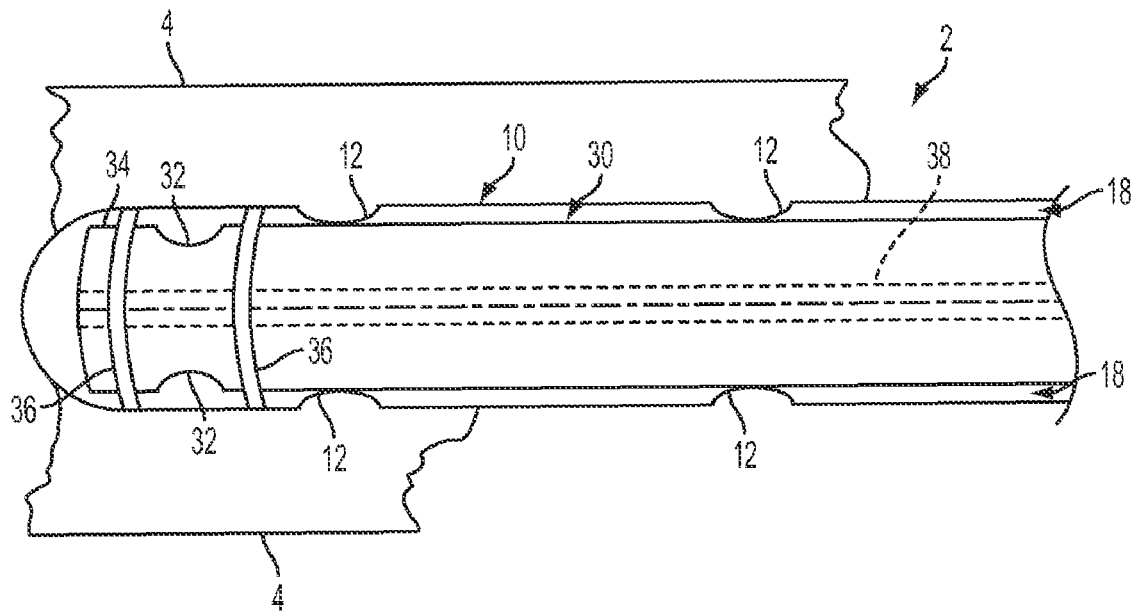
FIGS. 3(A)-(B) are schematic elevational views of a portion of a catheter having an outer catheter or tube disposed within an inner catheter tube wherein their respect apertures are misaligned and aligned, respectively.
Figure 3B:
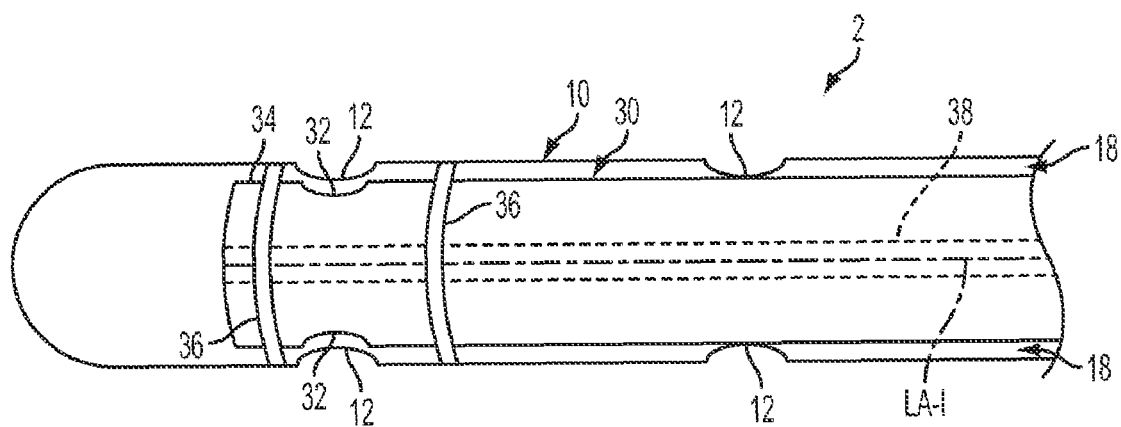

Referring to FIGS. 3(A)-3(B), the inner catheter 30 or inner tube may be inserted, removed, translated, or rotated within the outer catheter 10, and typically will be substantially coaxially aligned with the outer catheter 10 although that is not a requirement. The space between the outer wall of the inner catheter 10 and the inner wall of the outer catheter 30 is defined as an inter-tube gap 18. The inner catheter 30 has at least one or more apertures, such as port hole means 32, located circumferentially at or proximal to its distal tip/end/region 34. The distal tip/end 34 of inner catheter 30 has a sealing device or system 36 (or other structure to block the transference of a given medium) such as a plurality of circumferential gaskets located on either side of the aperture or port hole means 32. In one specific embodiment, the sealing device or system 36 might be similar to gaskets, o-ring seals or another type of annular means that projects above the surface of the inner catheter 30, coplanar with the surface of the catheter, below the surface of the outer catheter 10 or otherwise positioned within the inter-tube gap 18. Other examples of the sealing device or function may be provided by, but not limited thereto, the following: sleeve, grommet, bushing, annular rivet, snap closure, slip, pressure seal, elastic seal, pneumatic tension seal, collar, engaged seal, engaged joint, tab, offset, protuberance, shelf, ledge, extension, lip, bulge, collet, flange, thimble, or ring, knob, friction-fit communication between the inner tube and outer tube, elastic conformance, threaded-fit, bayoneted-fit, or other types of locking mechanisms or circumferential sealing devices or systems. Among the functions that may be provided by this sealing system is the reduced ability of materials to flow into and out of a hole in the outer catheter (tube), where such flow is not intended. For example, if there were a gap between the inner catheter (tube) and the outer catheter (tube), and holes in the inner catheter and outer catheter were aligned to allow diffusion of materials released from the inner catheter through the hole in the outer catheter, materials in the environment to which perfusion is to be effected could reflux into a space between the inner and outer catheters and materials trapped or located in that space between the inner and outer catheters could migrate or otherwise transfer into that environment or be released at another unintended time and location. One function of the seal system or device is to reduce any such unintended capture and/or release of materials, including materials present in space between the inner and outer catheter. The seal may also operate to reduce mass transfer of materials back into the openings in the inner and outer catheters, preventing other spurious concentration changes in materials to be delivered and/or reduce dilution of materials to be delivered and/or prevent spurious transport of materials from one environment to another environment by being picked up through transfer into space carried in or around the inner and/or outer catheter. As will be discussed later, for various embodiments the inner catheter 30 will generally have multiple inner chambers, channels or lumens each constituting a separate lumen of the device that communicates with an inlet on the proximal end/tip/region 35 (not shown) of the inner catheter 30. One example of such an inner chamber is shown as an intra-inner tube lumen 38. Referring to FIG. 3(A), the inner catheter 30 and outer catheter are shown positioned or located such that the inner catheter aperture(s) 32 and outer catheter aperture(s) 12 are not aligned in manner so as to prevent any transference of medium there through. For example, the medium could not be transferred or exchanged between the subject and the inner catheter/tube 30 via the pathway of the inner catheter apertures 32 and outer catheter apertures 12 combination. Alternatively, Referring to FIG. 3(B), the inner catheter 30 and outer catheter are shown positioned or located such that the inner catheter aperture(s) 32 and outer catheter aperture(s) 12 are at least partially aligned or congruent with one another such that a medium can be transferred between the inner tube 30 and the subject 4 via the pathway of the inner catheter aperture(s) 32 and outer catheter aperture(s) 12 combination. Some examples of medium that may be transferred from the inner tube to the subject may include, but not limited thereto, the following: therapeutic and diagnostic agents, for example, chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic and/or diagnostic agents, and other such substances.

Similarly, some examples of medium that may be transferred (i.e., withdrawn) from the subject to the inner tube may include, but not limited thereto, the following: edematous fluids, blood, cerebrospinal fluid, interstitial fluid, infected materials, neoplastic fluids and tissues, and other such substances.

It should be appreciated that the inner catheter tube 30 and outer catheter 10 tube may be comprised of a variety structures including, but not limited thereto, the following: constituting various types of conduits, channels, passages, pipes, tunnels, and/or bounded tubular surfaces or the like. Moreover, the tubes may have a variety of cross-sectional shapes including, but not limited to the following geometric shapes: circular, oval, multi-faceted, square, rectangular, hexagonal, octagons, parallelogram hexagonal, triangular, ellipsoidal, pentagonal, octagonal, or combinations thereof or other desired shapes, including variable diameter or cross-section geometries and irregular geometries.

Further, it should be appreciated that any of the apertures discussed herein may have a variety of shapes such as, but not limited thereto, the following circular, oval, multi-faceted, square, rectangular, hexagonal, octagons, parallelogram hexagonal, triangular, ellipsoidal, pentagonal, octagonal, or combinations thereof or other desired shapes.

Similarly, the apertures discussed herein may be of a variety structures such as, but not limited thereto, the following: recess, port, duct, trough, bore, inlet, hole, perforation, channel, passage, slot, orifice or the like.

Moreover, it should be appreciated that the various components of the inner and outer catheter may be a variety of commercially available materials used for all types of catheter systems. Some examples of materials used for the inner and outer catheters may include, but not limited thereto, the following: polymers, rubber, plastic, composites, metals, ceramics, hydrogels, dialysis membranes and other membranous materials, MR-compatible alloys and materials, and other organic and inorganic compounds and substances and the like. It should be appreciated that the various components of the catheter system 2, including but not limited thereto, the outer tube 10, sealing device 46 and inner tube 30 may be flexible or rigid and combination thereof as required or desired for intended use. Similarly, the catheter system 2, including but not limited thereto, the outer tube 10, sealing device 46 and inner tube 30 may provide volume contoured delivery/withdrawal (i.e., transfer) of a medium by adjusting its geometry and flexibility/rigidity according to the target location or anatomy (or region, including structure and morphology of any lesion) being treated.

Figure 4:
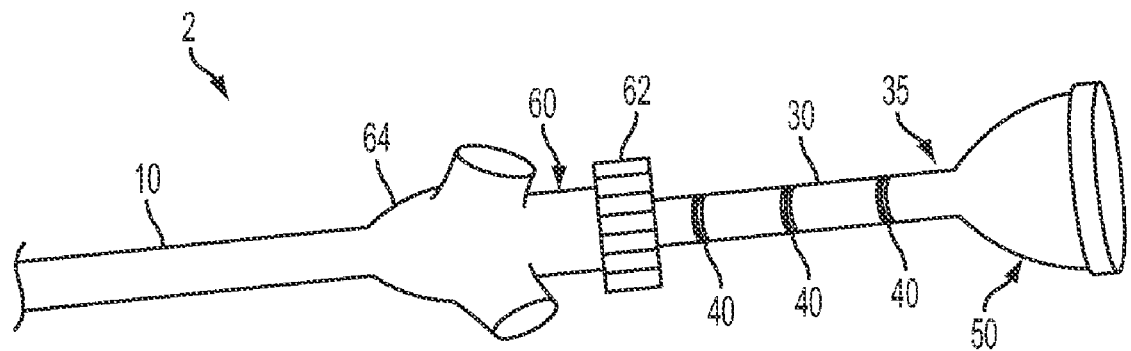
FIG. 4 schematically represents an embodiment of a coupling mechanism for the inner catheter or tube and outer catheter or tube device.

FIG. 4 schematically represents one specific embodiment of a coupling mechanism 60 that is within the generic scope of coupling mechanisms contemplated herein for the inner catheter 30 or inner tube and outer catheter 10 or outer tube means/device. In a simple exemplary form of this system, one version of the inner catheter 30 as shown, is fitted with a sequence of markings 40, each located at desired points, for example about 1 cm from the other, along the longitudinal axis, LA-I, of inner catheter 30. It should be appreciated that the distance between any of the points on the outer catheter or inner catheter may vary as desired or required. A port 50, such as a Luer port or the like (as well as other desired or required ports, manifolds, instruments or components) is located at the proximal end 35 of inner catheter 30, in order to fit a syringe or other fluid delivery or extraction device to the inner catheter 30. The inner catheter 30 may be slid or advanced into the outer catheter 10 through a coupling 60 or locking device, such as a screw-locking hub or the like having threaded cap 62 which can be tightened by hand onto a coupling hub base 64.

Figures 5A, 5B:
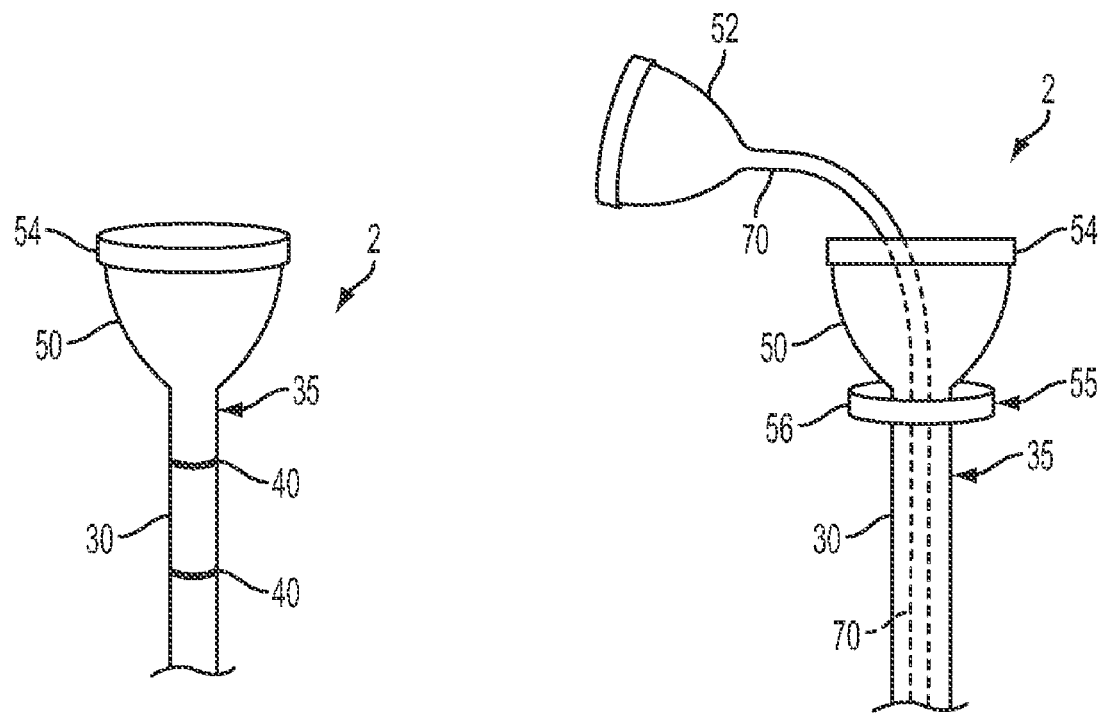
FIGS. 5(A)-(B) are schematic illustrations of a portion of the proximal end of the catheter device demonstrating exemplary embodiments of medium entry points or approaches for the inner catheter.

FIGS. 5(A)-(B) are schematic illustrations of a portion of the proximal end 35 of the catheter device 2 demonstrating exemplary embodiments of medium entry points or approaches for the inner catheter 30. Referring to FIG. 5(A), FIG. 5(A) is a schematic illustration of a partial portion of the inner catheter 30, wherein the upper lip of the port 50, e.g., Luer fitting, may have an extra seal 54 that is designed to provide an extra degree of certainty that there shall be no leakage when a delivery means (or retrieval means) such as a syringe is mated into the Luer port/means 50.

Referring to FIG. 5(B), FIG. 5(B) is a schematic illustration of an alternative embodiment wherein the Luer port/means 50 is provided so as to form an inner catheter hub 55. The inner catheter has a Luer port/means 50 that accommodates a second Luer port/fitting 52 that might be used to drive water, air or any other kind of liquid or gaseous fluid through internal flush line 70. In this particular embodiment, a fitting 56 has been added to the base of Luer port/fitting 50 to provide a means for holding the inner catheter upper hub assembly 55 tightly while fitting syringes or other fluid driver or extractor means into the Luer ports 50 and 52.

Figure 6A:
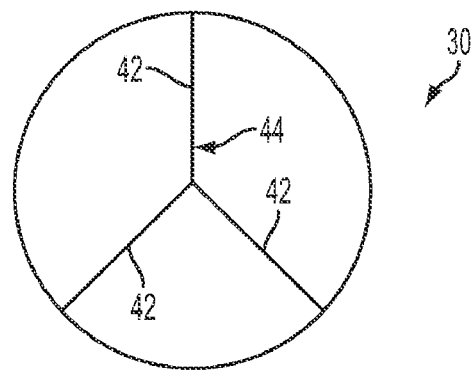

FIG. 6(A) provides a schematic elevational view from the distal end an embodiment of an inner catheter 30 in which the interior of the inner catheter 30 has been divided along its entire axial length (or at least a portion of its length as necessary to accomplish it's intended function) into three chambers 42 separated by a divider, wall or partition means 46. For example, one of the chambers 42 can server as the air-escape means, a second chamber 42 can serve as an agent delivery means, and a third chamber 42 can serve as a flushing channel means. It should be appreciated that the one or more chambers may be utilized as required or desired. Furthermore, other functions of these chambers (lumens or channels) may also include user-controlled constriction of the chamber, lumen or channel volume for the purpose of regulating or blocking a flow through the chamber, lumen or volume; simultaneous delivery of different agents or materials through a plurality of chambers, lumens or volumes to achieve mixing of the agents or materials upon delivery; transport of an agent or material between one chamber, lumen or volume and another one via an internal membranous structure in a dialysis-like or osmotic fashion; and the like.

Figure 6B:
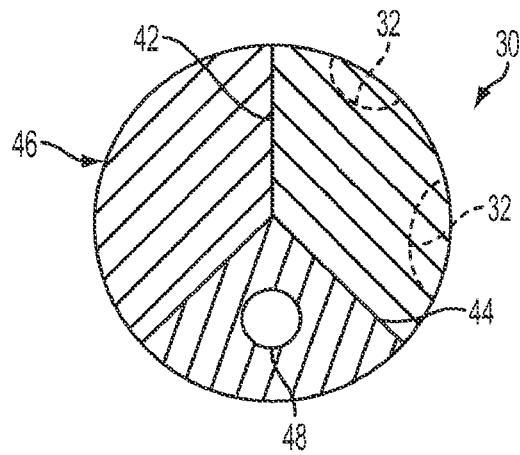
FIG. 6(B) is a schematic elevational view of the distal end of an embodiment the inner catheter, in which the distal tip/end of the inner catheter has a closure surface sealing the three chambers, except that an aperture is provided through the closure surface in one or more the chambers to serve as the air escape port (or other function) for the air trapped within the outer catheter.

FIG. 6(B) is a schematic elevational view of the distal end of an embodiment the inner catheter 30, in which the distal tip/end 34 of the inner catheter 30 has closure surface 46 sealing the three chambers 42, except that an aperture 48 is provided through the closure surface 46 in one of the chambers to serve as the air escape port for the air trapped within the outer catheter 10 by virtue, for example, the inner catheter 30 being inserted into (rotated or retracted from) the outer catheter 10.

Figure 6C:
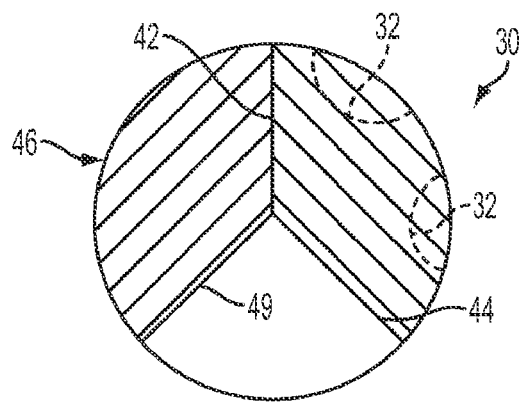
FIG. 6(C) is schematic elevational view of the distal end of an inner catheter means in which the aperture is an orifice formed at the distal end formed from the entire chamber to provide an air escape port (or other function).

FIG. 6(C) is schematic elevational view of the distal end 34 of an inner catheter means 30 in which rather than having aperture 48, as previously shown in see FIG. 6(B), that serves as the air escape means, instead an entire chamber of the distal end of 34 may be uncovered from closure surface 46, resulting in an orifice 49, in order to maximize the ease of escape of air trapped inside the outer catheter 10. For instance, air may be trapped inside the outer catheter as a result of the inner catheter 30 being inserted (rotated or retracted from) into the outer catheter 10.

Figure 7:
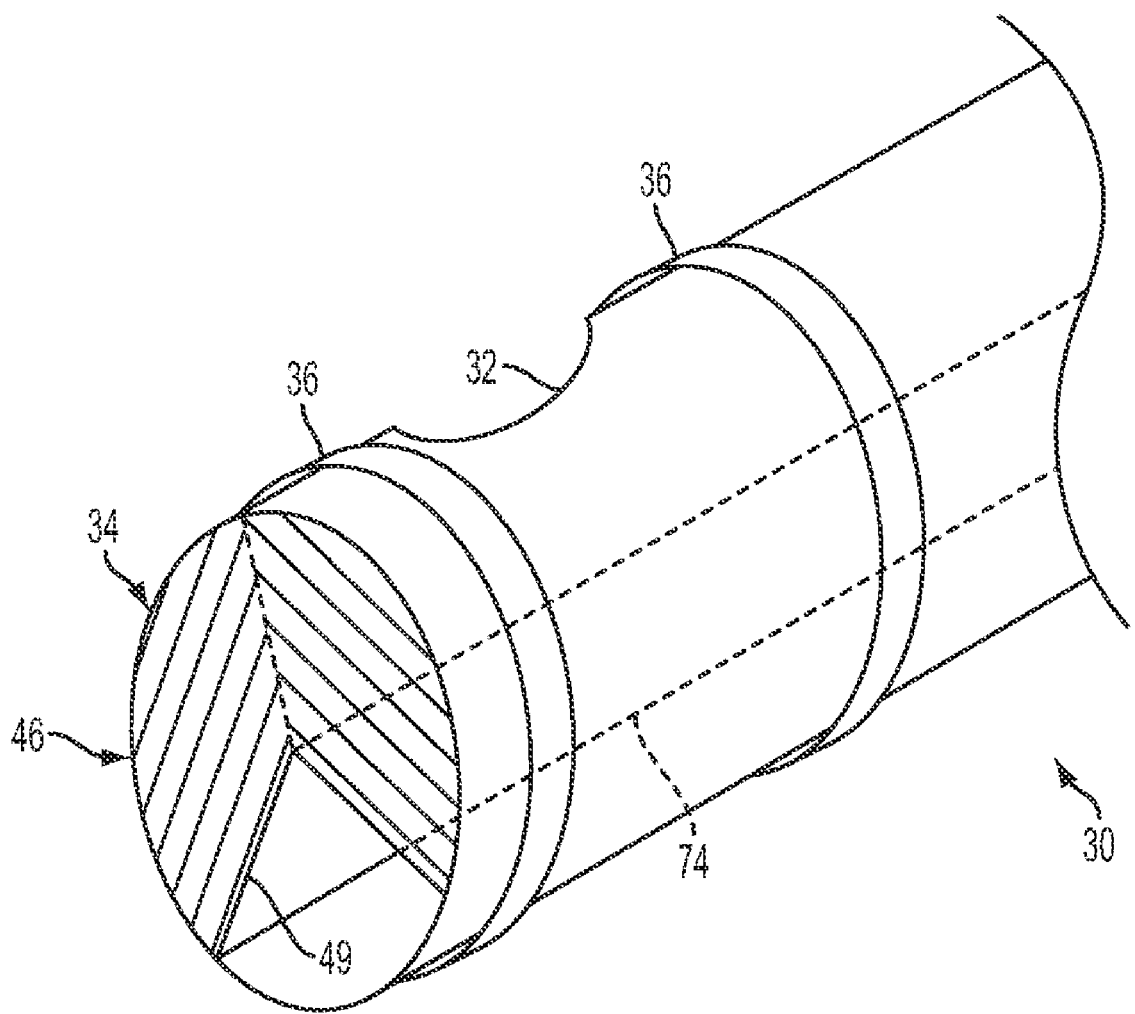
FIG. 7 shows a perspective schematic view of the distal tip of an inner catheter means in which a segment of the air escape channel is shown leading towards the proximal end (not shown) of the inner catheter device and away from the orifice of the distal end.

FIG. 7 shows a perspective schematic view of the distal tip 34 of an inner catheter means 30 in which a segment of the air escape channel 74 is shown leading towards the proximal end 35 (not shown) of the inner catheter device 30 and away from the orifice 49 of the distal end 34. Also shown is the orifice structure 49 and port hole structure/means 32 in relation to sealing device 36, such as a gasket means or the like.

Figure 8:
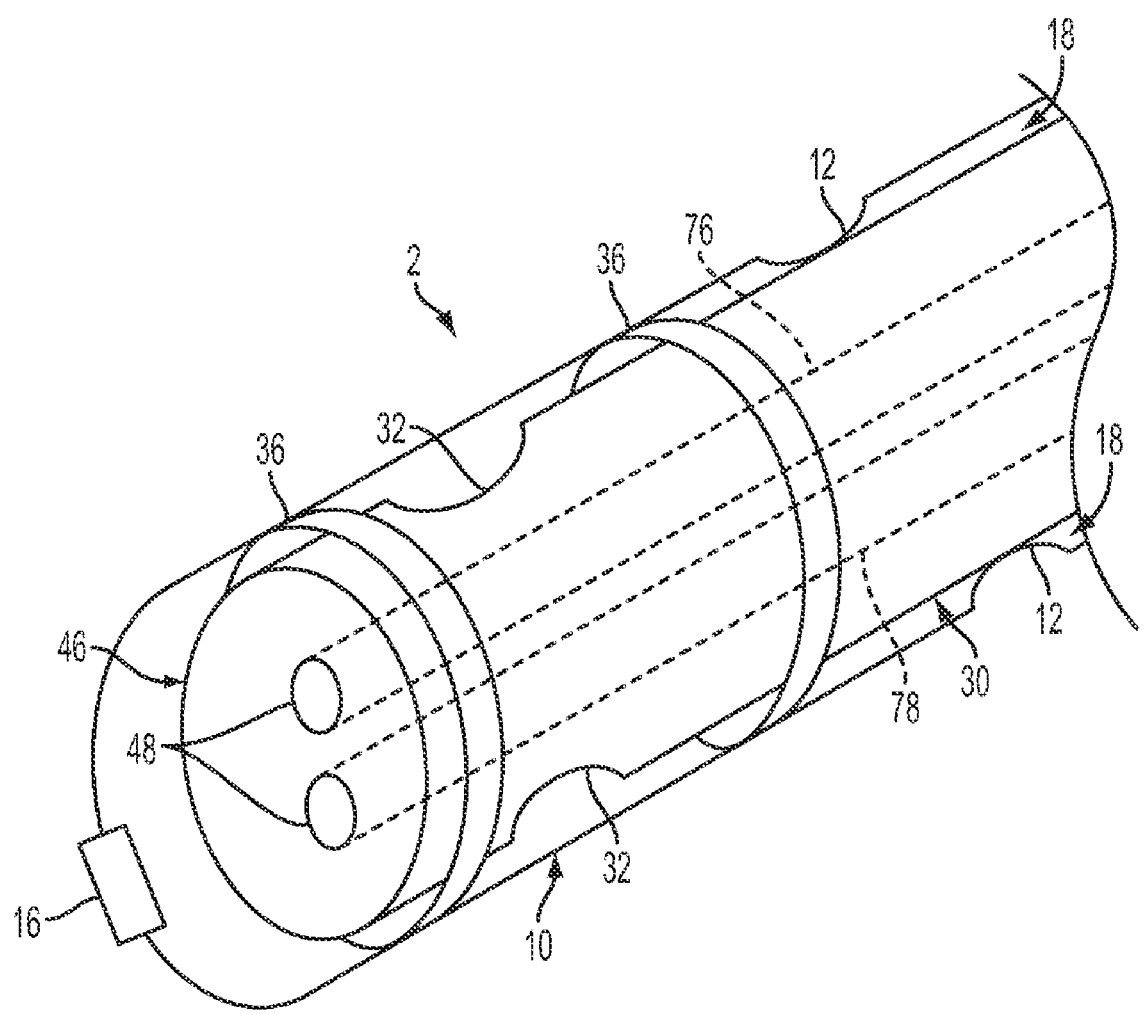
FIG. 8 is a perspective schematic view an alternative embodiment of a coupled inner and outer catheter combination, in which inner catheter has a longitudinal pattern of port holes, and further includes inner chambers that are in communication with the apertures on the closed surface of the distal end of the inner catheter.

FIG. 8 is a perspective schematic view an alternative embodiment of a coupled inner and outer catheter combination, in which inner catheter 30 has a longitudinal pattern of port holes 32, and further includes inner chambers 76 and 78 that are in communication with the apertures 48 on the closed surface 46 at the distal end of the inner catheter 30. As discussed earlier, the port holes 32 of the inner catheter 30 can be aligned circumferentially and/or longitudinally with port hole means 12 of the outer catheter means 10 such that an overlap allows an out-flow of a therapeutic agent, for example, toward the subject. A microcoil device 16, as generically shown, may be located at the tip of outer catheter means 10 to help enable high contrast magnetic resonance imaging or magnetic resonance spectroscopy measurement of species proximal to the tip of outer catheter 10 in a brain or other locations of a patient or subject. A plurality of the microcoil devices may be used on any combination of the catheter system 2 to best accomplish the magnetic resonance imaging or spectroscopy.

An example of a coil device 16, may be a radio frequency (RF) microcoil that may be wound circumferentially on the outer tube. An RF microcoil system may be wound circumferentially on both the outer tube and/or the inner tube. The physical and electrical characteristics of the RF microcoil elements are such as to enhance the contrast of magnetic resonance images made of body parts into which the catheter means incorporating the microcoil elements are inserted. Active MR visualization of drug, cell, and gene vector delivery can be achieved by means of one or more RF microcoils positioned on the catheter as disclosed in U.S. Pat. No. 6,026,316 to Kucharczyk et al. Single microcoils may be used separately or the combination of microcoils may be constructed in an array that may be used together to optimally image the surrounding environment, including the tissue structure and function within the field of response of the microcoils. The system of microcoils may, by way of non-limiting example, be used for very small (picoliter, nanoliter or microliter) injections measured within a solenoid volume RF microcoil, which by design is mainly sensitive to the volume inside the coil. The imaging volume in such a use is usually directly related to the diameter of the RF coil.

One skilled in the art can appreciate that many other embodiments of inner and outer catheter means, port hole means, inner chamber means, inner or outer tube gasket or sealing means, interconnection and hub means, micro coil means, and other details of construction constitute non-inventive variations of the novel and insightful conceptual means, system and technique which underlie the present invention.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A method for delivering at least one medium to a subject using a catheter device, wherein said method comprises:
    inserting an outer tube into the subject, said outer tube having a distal end and a proximal end and comprising at least one aperture there between;
    disposing an inner tube within said outer tube, such that a longitudinal space between said outer tube and said inner tube defines an inter-tube gap, said inner tube having a distal end and a proximal end and comprising at least one aperture there between;
    providing the at least one medium into said inner tube;
    aligning said outer tube aperture and said inner tube aperture to allow the at least one medium to travel through said inner tube aperture and outer tube aperture to the subject while controlling the medium from traveling between the exterior of said inner tube and interior of said outer tube;
    providing a seal in said inter-tube gap to control the medium from traveling within said inter-tube gap, wherein said seal controls travel of the medium in a distal direction beyond a distal portion of said seal, and in a proximal direction beyond a proximal portion of said seal.

2. The method of claim 1, wherein said controlling is a prevention of travel.

3. The method of claim 2, further comprising allowing trapped air inside said outer tube distal of the distal portion of said seal to escape when said inner tube is disposed into said outer tube via a passage included in said inner tube.

4. The method of claim 1, wherein said controlling comprises preventing the medium from traveling in the direction of the catheter proximal end and the distal end.

5. The method of claim 1, wherein said controlling is a reduction of travel.

6. The method of claim 5, further comprising allowing trapped air inside said outer tube distal of the distal portion of said seal to escape when said inner tube is disposed into said outer tube via a passage included in said inner tube.

7. The method of claim 1, wherein said controlling comprises reducing the medium from traveling in the direction of the catheter proximal end and the distal end.

8. The method of claim 1, further comprising allowing trapped air inside said outer tube distal of the distal portion of said seal to escape when said inner tube is disposed into said outer tube via a passage included in said inner tube.

9. The method of claim 1, wherein the medium being delivered comprises at least one of chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic and/or diagnostic or agents.

10. The method of claim 1, further comprising withdrawing a medium from the subject, said method comprising:
   aligning said outer tube aperture and said inner tube aperture to allow the at least one medium to travel from the subject through said outer tube aperture and inner tube aperture to the inner tube while controlling the medium from traveling between the exterior of said inner tube and interior of said outer tube.

11. The method of claim 10, wherein said controlling is a prevention of travel.

12. The method of claim 11, further comprising allowing trapped air inside said outer tube distal of the distal portion of said seal to escape when said inner tube is disposed into said outer tube via a passage included in said inner tube.

13. The method of claim 10, wherein said controlling comprises preventing the medium from traveling in the direction of the catheter proximal end and the distal end.

14. The method of claim 10, wherein said controlling is a reduction of travel.

15. The method of claim 14, further comprising allowing trapped air inside said outer tube distal of the distal portion of said seal to escape when said inner tube is disposed into said outer tube via a passage included in said inner tube.

16. The method of claim 10, wherein said controlling comprises reducing the medium from traveling in the direction of the catheter proximal end and the distal end.

17. The method of claim 10, further comprising allowing trapped air inside said outer tube distal of the distal portion of said seal to escape when said inner tube is disposed into said outer tube via a passage included in said inner tube.

18. The method of claim 10, wherein the medium being withdrawn comprises at least one of edematous fluids, blood, cerebrospinal fluid, interstitial fluid, infected materials, neoplastic fluids and tissues, and other such substances.

19. The method of claim 1, wherein said catheter is positioned under non-invasive imaging guidance.

20. The method of claim 1, wherein said catheter is positioned near a targeted area of treatment using non-invasive imaging guidance.

21. A method for withdrawing at least one medium from a subject using a catheter device, wherein said method comprising:
   inserting an outer tube into the subject, said outer tube having a distal end and a proximal end and comprising at least one aperture there between;
   disposing an inner tube within said outer tube, such that a longitudinal space between said outer tube and said inner tube defines an inter-tube gap, said inner tube having a distal end and a proximal end and comprising at least one aperture there between;
   aligning said outer tube aperture and said inner tube aperture to allow the at least one medium to travel from the subject through said outer tube aperture and inner tube aperture to the inner tube while controlling the medium from traveling between the exterior of said inner tube and interior of said outer tube; and
   providing a seal in said inter-tube gap to control the medium from traveling within said inter-tube gap, wherein said seal controls travel of the medium in a distal direction beyond a distal portion of said seal, and in a proximal direction beyond a proximal portion of said seal.

22. The method of claim 21, wherein said controlling is a prevention of travel.

23. The method of claim 22, further comprising allowing trapped air inside said outer tube distal of the distal portion of said seal to escape when said inner tube is disposed into said outer tube via a passage included in said inner tube.

24. The method of claim 21, wherein said controlling comprises preventing the medium from traveling in the direction of the catheter proximal end and the distal end.

25. The method of claim 21, wherein said controlling is a reduction of travel.

26. The method of claim 25, further comprising allowing trapped air inside said outer tube distal of the distal portion of said seal to escape when said inner tube is disposed into said outer tube via a passage included in said inner tube.

27. The method of claim 21, wherein said controlling comprises reducing the medium from traveling in the direction of the catheter proximal end and the distal end.

28. The method of claim 21, further comprising allowing trapped air inside said outer tube distal of the distal portion of said seal to escape when said inner tube is disposed into said outer tube via a passage included in said inner tube.

29. The method of claim 21, wherein the medium being withdrawn comprises at least one of edematous fluids, blood, cerebrospinal fluid, interstitial fluid, infected materials, neoplastic fluids and tissues, and other such substances.

* * * * *